United States Patent
Lackas et al.

(10) Patent No.: US 7,498,580 B2
(45) Date of Patent: Mar. 3, 2009

(54) TOMOGRAPHIC DEVICE AND METHOD WITH TRANSLATIONAL MOVEMENT BETWEEN OBJECT AND DETECTOR

(75) Inventors: Christian Lackas, Aachen (DE); Nils Schramm, Aachen (DE); Uwe Engeland, Göttingen (DE)

(73) Assignee: Forschungszentrum Julich GmbH, Gottingen (DE)

( * ) Notice: Subject to any disclaimer, the term of this patent is extended or adjusted under 35 U.S.C. 154(b) by 0 days.

(21) Appl. No.: 10/576,933

(22) PCT Filed: Oct. 18, 2004

(86) PCT No.: PCT/DE2004/002310

§ 371 (c)(1),
(2), (4) Date: Feb. 21, 2007

(87) PCT Pub. No.: WO2005/040635

PCT Pub. Date: May 6, 2005

(65) Prior Publication Data

US 2007/0215811 A1     Sep. 20, 2007

(30) Foreign Application Priority Data

Oct. 21, 2003   (DE) ................... 103 48 868

(51) Int. Cl.
*G01T 1/166*   (2006.01)
(52) U.S. Cl. .............. 250/363.04; 250/363.1
(58) Field of Classification Search ........... 250/363.03, 250/363.04, 363.05, 363.1
See application file for complete search history.

(56) References Cited

U.S. PATENT DOCUMENTS

| | | | | |
|---|---|---|---|---|
| 4,144,457 A | * | 3/1979 | Albert | 378/9 |
| 4,419,585 A | * | 12/1983 | Strauss et al. | 250/505.1 |
| 5,107,121 A | | 4/1992 | Lim et al. | |
| 6,147,352 A | | 11/2000 | Ashburn | |
| 6,445,767 B1 | * | 9/2002 | Karellas | 378/98.8 |
| 7,199,371 B2 | | 4/2007 | Schramm | 250/363.04 |

FOREIGN PATENT DOCUMENTS

| | | |
|---|---|---|
| DE | 101 42 421 | 4/2003 |
| EP | 0 846 961 | 6/1998 |
| GB | 1 184 304 | 3/1970 |

OTHER PUBLICATIONS

"High-Resolution SPECT Using Multipinhole Collimation" *IEEE Transactions on Nuclear Science*, vol. 50, No. 3, Jun. 2003.

* cited by examiner

*Primary Examiner*—David P Porta
*Assistant Examiner*—Mark R Gaworecki
(74) *Attorney, Agent, or Firm*—Andrew Wilford

(57) ABSTRACT

The invention relates to a device for carrying out a tomographic method, in particular for carrying out single-photon tomography, with at least one multi-hole collimator and at least one detector, for recording photons which pass through the multi-hole collimator. The above is characterised in comprising means which permit a relative translational movement between an object under investigation and the detector(s) with a positional accuracy of less than 1 millimeter. The relative positional change between object and detector(s) during the execution of the method is taken into account in the subsequent reconstruction method to an accuracy of less than 1 mm, in particular, less than 0.1 mm. A reconstruction method is used for the above which takes into account the positional and angular information between object and detector. Said method may be controlled by and carried out on a current PC.

13 Claims, 3 Drawing Sheets

TOMOGRAPHIC DEVICE AND METHOD WITH TRANSLATIONAL MOVEMENT BETWEEN OBJECT AND DETECTOR

CROSS REFERENCE TO RELATED APPLICATIONS

This application is the US national phase of PCT application PCT/DE2004/002310, filed 18 Oct. 2004, published 6 May 2005 as WO 2005/040635, and claiming the priority of German patent application 10348868.5 itself filed 21 Oct. 2003 whose entire disclosures are herewith incorporated by reference.

BACKGROUND OF THE INVENTION

The invention concerns a device as well as a tomographic method, in particular for single-photon (emission) tomography (SPECT).

Single-photon tomography as well as its devices relates to a method of three-dimensional imaging of radiopharmaceuticals inserted in an object. Such objects are in particular persons, animals, plants or parts thereof, as well as inanimate objects.

The radiopharmaceuticals inserted in the object emit photons that are detected and analyzed by the device. As a result of the analysis the position, that is the spatial distribution of the radiopharmaceuticals in the object, is displayed. The position of the radiopharmaceuticals in turn allows conclusions on the object, as for example on a distribution of tissue in the object.

A common device for carrying out a SPECT comprises a gamma camera as detector and an upstream collimator. In general the collimator is a plate composed of a material with a high absorption coefficient and a large number of channels running perpendicularly through the plate. Providing these channels guarantee that only perpendicularly entering photons are detected so that analyzing the local resolution is possible.

SPECT and Positron Emission Tomography (PET) are instruments for the quantitative and in vivo display and reconstruction of spatial radiotracer distribution. Outside of human medicine these methods can be used to develop and evaluate novel tracer combinations in pharmacological and preclinical research. While in PET, various systems for the examination of small laboratory animals are available, such developments so far were insufficient in the field of SPECT, even though TC-99m and I-123 labeled radiopharmaceuticals are of much higher importance in nuclear medicine than PET nuclides.

In order to improve the local resolution and sensitivity of SPECT a hole collimator is used. A hole collimator is characterized by one single hole in the collimator plate through which photons pass. If the object is located closer to the hole collimator than the surface of a gamma camera or detector, a higher resolution of the object can be achieved. The photons do not pass through the hole collimator in an exclusively perpendicular way, but are displayed by an advantageously enlarging central geometry. Thereby a reconstructed resolution that is advantageously distinctly smaller than the detector's own resolution can be achieved.

The photons pass the hole collimator through a small opening, or hole in order to achieve a good local resolution. The smaller the hole, the less photons pass through that hole. Hence the sensitivity of the device is disadvantageously reduced with an increasingly smaller hole. Sensitivity is defined as relationship between the measured counting rate and the activity in the object. If the sensitivity decreases too much, no SPECT imaging can be performed any more. Increasingly smaller holes result in an advantageously smaller local resolution so that regarding the size of the holes a compromise between sensitivity and local resolution has to be found.

A device with a multi-pinhole collimator and detector to register photons passing through the multi-pinhole collimator is known from the DE 101 42 421 (U.S. Pat. No. 7,199,371). The collimator thus has several openings. Hence the distribution of radiopharmaceuticals can be measured with high resolution and high sensitivity. Different distributions of the radiopharmaceuticals in the object are estimated using an iterative reconstruction method, consequent measurement results are calculated that would cause the estimated distributions and as reconstruction result the estimated distribution whose calculated measurement result mostly coincides with the obtained measurement result is selected.

Camera and collimator rotate around the object during SPECT examinations (R-SPECT). The detectors characteristically surround the object with a given radius in 6 degree intervals so that 60 projections for all detectors for one sequence are obtained. In addition to the projections and the angle indication of the detectors changing relatively to the object, the rotation radius of the detectors rotating around the object is a further relevant parameter for the reconstruction. This rotation radius remains constant throughout the whole measurement procedure.

If small objects, mice for instance, are examined, it is also possible to rotate them around their axes and to keep the one or more detector(s) as well as their collimators fixed.

Such methods are of an observational accuracy of approx. 1 millimeter or $\frac{1}{10}$ degree.

Thanks to SPECT-examinations a high amount of projection data is available. The information received regarding the object allows an analysis of the position of the radiopharmaceuticals in the object. Functional conclusions for example regarding the coronary blood flow or the receptor density in the brain can then be drawn from the reconstructed, three-dimensional activity patterns.

A disadvantage is the mechanical system for positioning of the detectors, as the mass of detectors can weigh 100 kg and more. The necessary data of some organs that are hard to access can only be obtained under difficult circumstances and with poor results.

A disadvantageous impact on small animals rotating around their own axis consists in the fact that physiological stress in inflicted upon the animal. Furthermore the displacement of soft tissue inside the animal has to be compensated.

OBJECT OF THE INVENTION

It is therefore the object of the invention to provide a high-resolution and high-sensitive tomographic method that can be used for an easy examination of body regions that are hard to access.

It is further on the object of the invention to provide a high-resolution and high-sensitive tomographic method.

SUMMARY OF THE INVENTION

The object is realized by a device having means to provide a relative straight-line movement between an object under investigation and the one or more detector(s) (T-SPECT).

Instead of navigating heavy detectors around the object during the procedure that has the disadvantage that access from all sides is required, a straight-line movement is carried out, where either the light object conducts a straight-line movement through the field of view of the one or more detector(s) or the straight-line movement is carried out relative to the object by the one or more detector(s). Projection images are recorded from a series of positions and combined into a sequence. In addition to the projections the sequence also comprises data concerning the relative position between object and detector, as well as optionally a rotation radius.

If the device comprises only one detector, the object under investigation has to be freely accessible from one side only.

If the device comprises two detectors, especially if they are aligned orthogonally to each other, the object accordingly has to be freely accessible from two sides.

Instead of the object the one or more detector(s) can provide a straight-line movement relative to the object, which is of advantage for the application, especially for applications in human medicine.

Instead of by the object, the relative straight-line movements can also be carried out by the one or more detector(s) which is of advantage for the applications, in particular for applications in human medicine.

Furthermore combinations of both movements are possible, that means straight-line movement and rotational movement of object and detector.

In contrast to R-SPECT a T-SPECT comprises two more parameters per unit.

The use of tilted holes is particularly advantageous, as that way the object is already seen by every detector from different directions, without having to carry out a complete rotation. Due to that fact even with the use of one single detector different perspectives are explored and thus a more exact depth information is gained.

The expression means covers all parts of a tomograph providing a straight-line movement of the object and/or the one or more detector(s).

In one specific design of the invention the device provides a relative straight-line movement between the object under investigation and the one or more detector(s) with a positional accuracy of less than 1 millimeter, in particular with an accuracy of less than 0.1 millimeter.

Thereby, in combination with a adequate reconstruction method, a high-resolution and high-sensitive tomography, with a simplified structure, of body areas otherwise very hard to access, is made possible.

Thanks to the strong distance and angle dependence of the imaging system of the central geometry in the multi pinhole system a simple straight-line movement, relative between object and detector is enough to gain sufficient information for a reconstruction.

Another advantage is that the means provide straight-line movements in more than one direction in space, if required in all three directions in space, that means in direction X, Y and Z. Thereby the means can be configured in such way that they provide straight-line movements simultaneously in all three directions in space, with the advantageous result that time can be saved regarding the positioning of the object in relation to the one or more detector(s).

In the particularly advantageous case the positioning of the means is automatic. A PC can thereby control the straight-line movement of the one or more mean(s), coordinate the movement with the measurement procedure and if necessary analyze the gained information for reconstruction calculations.

It is possible to configure one or, if necessary, more detector(s) in such way that the detectors themselves carry out the straight-line movements. Thus the detector supports for instance are used as means providing a straight-line movement of the detectors. In addition to that the one or more detector(s) can also carry out rotational movements in one design of the invention.

A further advantageous design of the invention makes it possible to configure an object under investigation in such way that it carries out the straight-line movement. The support can comprise a table that can be moved on tracks.

The object is moved through the field of view of the one or more detector(s) on the table along three linear axes. The acceleration of the movement can be realized in such a gentle way that tissue displacements in the object are of no importance.

The straight-line movement is stopped in certain positions along the path in order to carry out a measurement.

If all the detectors are contemporaneously fixed the device-related extensive positioning of the heavy detectors according to the state-of-art is not necessary and costs are reduced thanks to the simpler design of the device.

It is possible that e.g. the support of the object carries out a straight-line movement and the one or more detectors carry (ies) out a coupled straight-line and/or even a rotational movement.

Then, as an especially advantageous result, body areas that are hard to access, as for instance the thyroid gland, can be examined by positioning the means of a tomographic examination in one work step, that means without manual new positioning of the detectors or the table.

Every projection is saved with the relative position of the object to the detectors and a possible rotation angle and attributed to the projection image. The number of necessary projection data and the measurement time of a T-SPECT system are still comparable to those of a R-SPECT system according to the state-of-the-art. The time period in which the straight-line movement is carried out is short compared to the measurement period.

The support for the object under investigation advantageously comprises a 3 axes table or a support that can carry out straight-line movements during the examination procedure.

The table can be moved, e.g. on tracks. The object under investigation is on the table. The tracks are arranged in such way that movements on linear axes in the point of view of the camera, if necessary in all three directions in space are rendered possible.

It is of particular advantage if the support is tiltable. The support is tilted parallel to the surface of the one or more detector(s).

Thereby the position of the object in relation to the collimator and to the camera can be changed marginally. Thus additional information from a different direction is gained in the projections, which results in an improved depth information.

A rotational movement of the support or of the one or more detector(s) thus can also consist of a tilting process.

The distance between object and multi-pinhole collimator can be advantageously smaller than the distance between the multi-pinhole collimator and the surface of the detector, in order to achieve an enlargement on the detector's surface.

Advantageously the device comprises two detectors orthogonally arranged to each other. Thus both detectors provide maximally different information. This results in a very well reconstructed resolution and a high sensitivity despite of an extremely simple device configuration. Costs are thus reduced.

The multi-pinhole collimators have double conical-shaped holes directed at the interior. It is especially advantageous if the holes have a so-called keel-edge design, with an opening angle considered in the following reconstruction algorithm. Keel-edge holes have parallel to each other a short cylindrical duct between the cones.

Characteristically seven to ten holes or pin-holes per multi-pinhole collimator are used.

Each hole registers a part of or the complete object. All holes together cover the whole volume under investigation in the object. It is of particular advantage if the axes of the holes are tilted in axial and/or transaxial direction so that the object is detected by every detector even without rotation from slightly different angles already.

The projections of the object through the holes overlap on the detector behind and thus cause an information multiplex. In addition to areas with simple overlapping, multi overlapping is also possible according to the collimators' design. This method permits a better use of the very limited detector surface. Thereby too strong overlapping is avoided as every overlapping makes the assignment of the projection images to the holes less unambiguous and results in a loss of resolution.

On the other hand, with a 7-hole collimator the rate of overlapping is 30-50%.

The algorithm for the reconstruction method operates with an optional amount of multi-pinhole projections and can reconstruct of the estimated activity distribution of these projections. Thereby it is always the relative position and the relative angle between object and the detectors that are considered, while established reconstruction methods always operate with stable rotation angles. The method according to the invention thus furthermore considers possible changes of position between the object and detectors.

In addition to a simpler mechanic design, the T-SPECT according to the invention can also be used if the object is not accessible from all sides. A detector system that comprises e.g. two detectors orthogonally arranged to each other, has to be able to register the object from two sides only.

For examinations of the thyroid the upper part of the patient's body can be surrounded in an ellipse, in order to constantly be as close as possible to the thyroid or to record the patient from two sides only. T-SPECT examinations with one detector only provide images whose results considering the depth information are significantly better than comparable planar images without these information.

With two detectors that are aligned orthogonally to each other forms are continuously undistorted and the resolution is increased, as well as a further improved depth information is gained.

For a further improvement of sensitivity and resolution three detectors can be used in a 120° geometry or in a different configuration. It thereby has to be considered that resolution and sensitivity at the side pointed at the detectors are significantly higher than at the other side. Reconstructed resolutions of less than 2 millimeters with medium sensitivities of 800 cps/MBq are possible.

While the method is carried out the relative position between object and detector(s) is changed with an accuracy of less than 1 millimeter, in particular with an accuracy of less than 0.1 millimeter.

The projections measured are processed with an iterative reconstruction algorithm, e.g. based on the Maximum Likelihood Expectation Maximization (MLEM). In order to determine the system matrix of the imaging system a model based on the ray-tracing method is used to determine the image function of each voxel of the object's volume and every hole. Thereby a small area surrounding each hole is scanned starting from each voxel and the sensitivity is calculated considering the absorption in the diaphragm and crystal, as well as the image geometry with which each pixel on the detector registers the corresponding voxel. The half-breadth of the spot on the detector is analogously determined. These data are precalculated according to table charts and used in the reconstruction program. Due to the straight-line movement, the effective volume the image function is calculated for, is enlarged, so that the table charts are optionally calculated for a less detailed raster and are calculated by trilinear interpolation for all voxel. Typical values thereby are voxel edge lengths of 0.3 mm in the objective's volume and 0.6 mm in the table charts. The data volume thereby decreases by a factor of 8 with a hardly verifiable degradation of the result, so that the algorithm can be efficiently used on common PCs.

A device according to the invention therefore comprises a data processing unit, e.g. a PC. The PC processes the data and is programmable. A computer program product renders it possible that the method is carried out in the device.

The calculation can be carried out as follows:

1. Calculation of the sensitivity by means of ray tracing technology and the half-breadth of the pictures for each voxel in the target volume.

2. Calculation of the forward projection from the data concerning sensitivity and half-breadth for the currently examined object through each hole in consideration of the position and angle with which the projection has been recorded.

3. Calculation of revision data from the comparison of measured and calculated projections 4. Application of the revision data to the current object and repetition of steps 2 and 3, or stop, if the wanted result is achieved.

The straight-line movement and/or the reconstruction method can be controlled with particular advantage on a PC.

If necessary an attenuation adjustment and an acceleration of the iteration can be carried out by a limiting to projection subsets (ordered subsets).

To calculate the sensitivity the surrounding areas of each hole are scanned starting from each voxel by rays (preferably 100) and thereby the cutting length, that is the length of the material duct in the diaphragm for the photons on their way to the detector is calculated. The holes are modeled in keel-edge form, that means with two double cones and a duct in between them. Thus every overlapping with the two detector surfaces, the surfaces of the two cones and the duct is considered. Thereby the axis of a hole can be optionally tilted in axial and transaxial directions.

The half-breadth is estimated with the help of the image geometry, assuming that the voxel are imaged in a gauss-shaped manner. This assumption is true for voxel that are close by the perpendicular bisector of the detector. It is as well sufficiently exact for voxel imaged under bigger angles. Thereby the intrinsic resolution of the detector, that is the resolution without collimator, is taken in consideration.

In order to efficiently save the two table charts, one or more reference table(s) is/are created for each table chart. Here the possible data is indicated and encoded in one byte (8 bits).

During reconstruction the data for the object's volume are interpolated trilinearly from the table charts. This can be done either with every access to the table chart or optionally once before starting for the whole target volume.

For the reconstruction the table charts for sensitivity and half-breadth for all diaphragms and holes are loaded, as well as the projection and measurement data containing the position and angle of the object or the detector.

A starting object (e.g. cone homogeneously filled with radiopharmaceuticals) is determined and chosen as first target volume and an iteration is carried out.

The iterations are stopped when the wanted result is achieved.

The algorithm guarantees that the likelihood function increases with every step, thus the probability increases that the calculated target volume generated the measured projections.

Instead of always applying the iterations to all projections simultaneously, they can also be applied to a subset only. For instance 60 projections are divided into 12 groups of 5 projections per group and subiterations with only 5 projections in each group are carried out. Thus adjustments are carried out more frequently and hence the object's volume quicker approaches the final result. The number and size of the groups vary; it is especially advantageous to decrease the number of groups during later iterations so that towards the end of the reconstruction more and more projections contribute to the revision data.

The result can be further improved by a orthogonal permutation of the groups.

BRIEF DESCRIPTION OF THE DRAWING

In the following the invention is to be further explained by means of a drawing in which.

SPECIFIC DESCRIPTION

Figure 1:
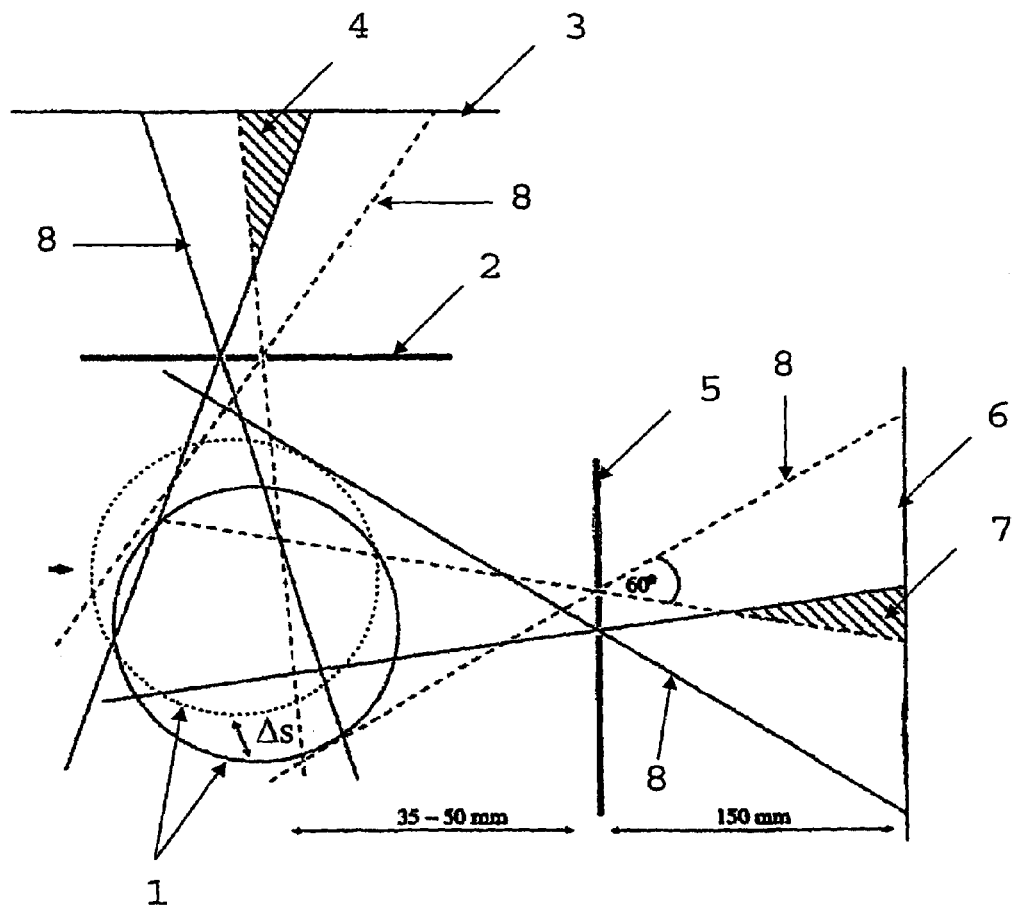
FIG. 1 is a diagram illustrating the invention.

The basic structure of a device with two detectors, orthogonally aligned to each other, each respectively consisting of a multi-pinhole collimator 2, 5 and detector surface of the gamma camera 3, 6 is illustrated in FIG. 1.

The object 1 is located closer to the multi-pinhole collimators 2, 5 than the detector surface 3, 6. The multi-pinhole collimators 2, 5 have holes that discharge into the collimator 2,5 in a funnel-shaped way from both sides (not illustrated), in order to thereby provide the passing through of diagonally impinging photons through the holes. Per collimator two holes (no reference sign) are illustrated that are passed by the photons 8.

The holes have a keel-edge design. Photons 8 leaving the object pass through the holes of the collimators 2, 5 toward the detector surface 3, 6. Thus the object 1 is reproduced on the detector surface 3, 6 in an enlarged version.

There are overlapping areas 4, 7 on the detector surface 3, 6 between the single cones formed by the photons 8 according to the straight-line movement (Ds) of the object 1.

Figure 2:
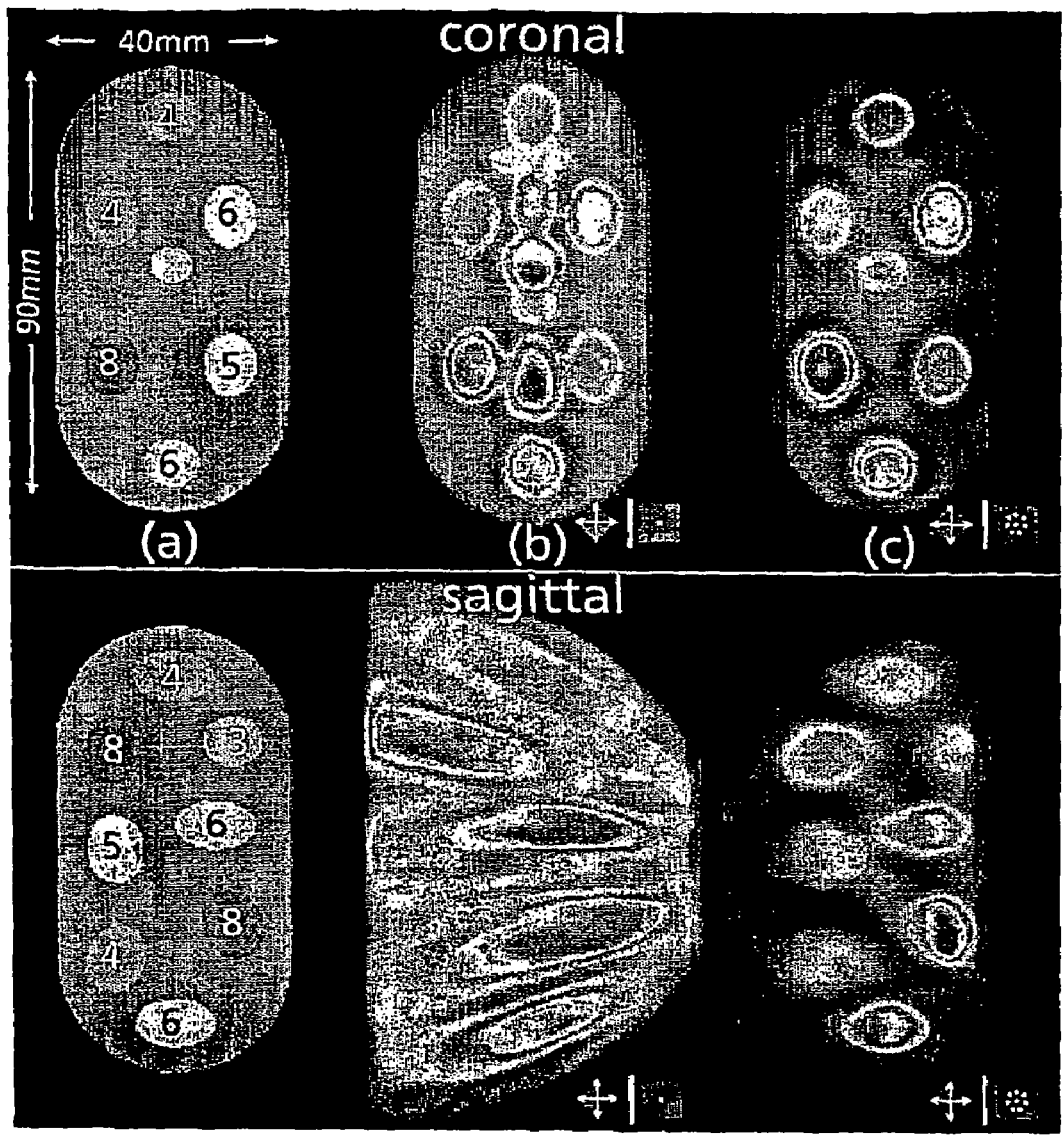
FIGS. 2a-2c are cross sections seen according to the invention.

FIGS. 2a-c illustrate coronary (upper row) and sagittal (lower row) cross-sectional views on a phantom (2a), a reconstruction with one detector only and a hole in the diaphragm (2b) and with one detector and seven holes (2c).

The numbers in the phantom are an indication for the activity in the hot spots. The phantom is a homogeneously filled cone with rounded caps containing 12 hot sources with elevated activity.

The coronary cross sectional views provide better results as the detector is perpendicularly pointed at this level and thus contains maximum information.

In the cross sectional view of FIG. 2b the depth information is missing as the one hole registers the phantom only from one side exactly. Thus the sagittal cross sectional view is distorted and some points are difficult to resolve in sagittal direction. In the coronary cross sectional view, sources from other levels show through the luting in sagittal direction.

Then again the seven tilted holes from FIG. 2c already provide very good results at coronary level with one detector only. In the sagittal cross sectional view all the hot spots in the phantom can already be detected and separated, but the reconstruction stills shows some artifact distortions. Hence T-SPECTS with seven tilted holes and one detector already provides useful 3-d information regarding the activity distribution and therefore is highly superior to planar images according to the state-of-the-art.

Figure 3:
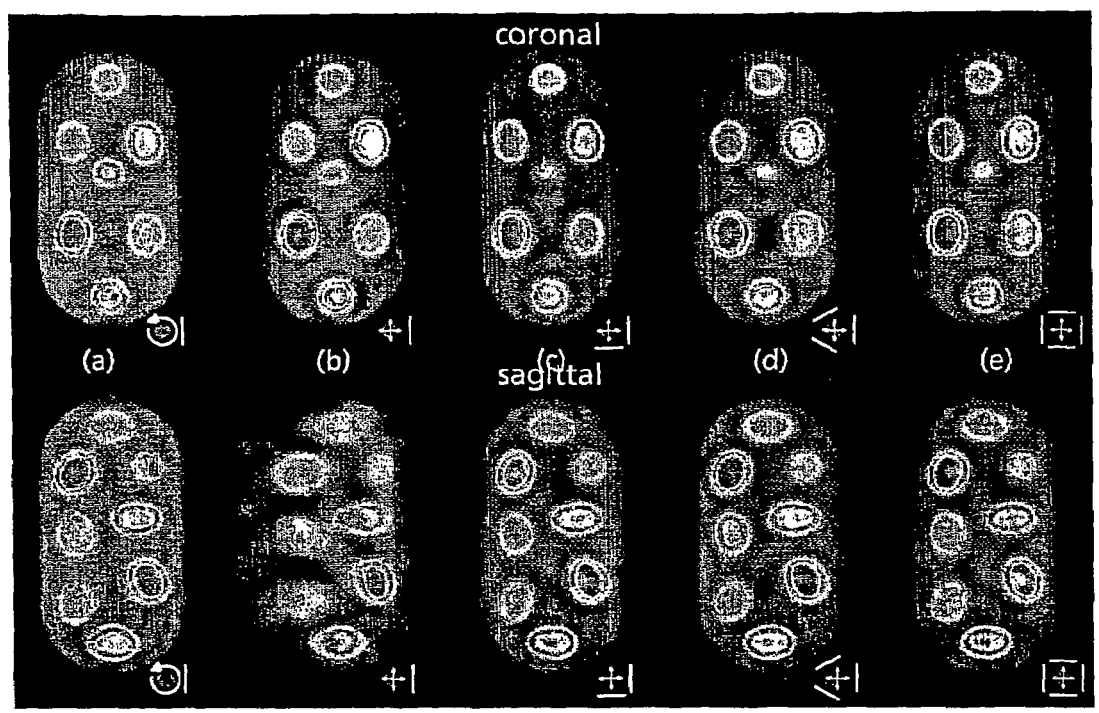
FIGS. 3a-3e are further sections according to the invention.

FIGS. 3a-e show a reconstruction of the same phantom as illustrated in FIGS. 2a-c. All images of FIGS. 3a-e have been recorded with the same 7-hole diaphragm but with different numbers of detectors. In comparison FIG. 3a shows the result of a common R-SPECT, depicted by the rotation symbol.

Thereby the result form FIG. 3a is very good, except for the two pointed caps. This artifact is characteristic for R-SPECT, as the object is not moved toward the rotation axis (Z-axis).

FIG. 3b shows the coronary and sagittal cross sectional views known from FIG. 2c with one detector only.

FIGS. 3c and 3e show corresponding coronary and sagittal cross sectional views with two detectors orthogonally aligned to each other (FIG. 3c), with three detectors aligned to each other in a distance of 120° (FIG. 3d) and with four detectors aligned to each other in a distance of 90°.

If these figures are compared it becomes clear that 2 detectors (FIG. 3c) are already enough to gain sufficient depth information, in order to reconstruct the phantom in a very high quality. Further detectors improve the sensitivity of the system so that shorter measurement times with the same expected result can be achieved.

Dependent on application case and target, especially resolution and measurement time, the device according to the invention can be thus adapted.

For FIG. 3a altogether 60 R-SPECT projections with a rotation radius of 50 millimeter have been recorded by a camera.

For the T-SPECT images the same number of projections was used that means 60 projections with one detector, 30 projections each with two detectors, 20 projections with three and with four detectors 15 projections each were recorded. Thereby the position of the object has been changed by a straight-line movement in a distance of 50 millimeter in direction X/Y up to 10 millimeter and in direction Z up to maximum 5 millimeter.

The invention claimed is:

1. A device for carrying out a tomographic method with at least one multi-pinhole collimator and at least one detector for recording photons passing through the collimator, the device comprising:
   a support holding an object at a spacing from the multi-pinhole collimator that is smaller than a distance between the multi-pinhole collimator and a surface of the detector such that photon-generated images partially overlap on the detector's surface,
   means for tipping holes of the collimator transaxially or axially toward the object or parts thereof; and
   means for relatively shifting the object and the detector in a straight-line movement while carrying out the method.

2. The device defined in claim 1 wherein the means for shifting can be positioned with an accuracy of less than 0.1 mm.

3. The device defined in claim 1 wherein the means for shifting is automatic.

4. The device defined in claim 1 wherein the support is tiltable parallel to the detector's surface.

5. The device defined in claim 1 wherein there are two of the detectors that are orthogonally aligned to each other and stationary.

6. The device defined in claim 1 wherein the holes of multi-pinhole collimators are conical.

7. The device defined in claim 1 wherein the holes are keel-edged.

8. The device defined in claim 1, further comprising:
data-processing means for carrying out a reconstruction method.

9. A method of carrying out a tomographic method with a device according to claim 1 comprising the steps of:
setting spacings between the holes in the multi-pinhole collimator and a size and position of the object such that photon generated images partially overlap on the detector's surface,
changing the relative position between the object and detector with straight-line movement of the object or of the detector,
using holes of the collimator that are tilted transaxially or axially toward the object or parts thereof, and
carrying out a reconstruction method considering the position between detector(s) and object and considering each individual hole geometry and hole tilt in axial and transaxial direction such that different perspectives of the object are explored and thus depth information of the object is augmented by repeatedly changing the relative position between object and detector by straight-line movement of the object or detector.

10. The method defined in claim 9 wherein the relative position between an object and detector is changed with an accuracy of less than 1 mm.

11. The method defined in claim 9 wherein the detector or the object are shifted in a straight line or rotationally.

12. The method defined in claim 9 wherein the reconstruction method is modeled on a PC.

13. A computer program on a computer readable medium provided to interact with a data processing unit such that the data processing unit performs the reconstruction method defined in claim 9.

* * * * *